(12) United States Patent
Cavinato et al.

(10) Patent No.: US 11,786,462 B2
(45) Date of Patent: Oct. 17, 2023

(54) PARACETAMOL LIQUID SUSPENSIONS

(71) Applicant: GSK Consumer Healthcare S.A., Prangins (CH)

(72) Inventors: Mauro Cavinato, Nyon (CH); Karin Gerola, Nyon (CH)

(73) Assignee: GSK CONSUMER HEALTHCARE SARL, Prangins (CH)

( * ) Notice: Subject to any disclaimer, the term of this patent is extended or adjusted under 35 U.S.C. 154(b) by 0 days.

(21) Appl. No.: 17/269,063

(22) PCT Filed: Aug. 22, 2019

(86) PCT No.: PCT/EP2019/072445
§ 371 (c)(1),
(2) Date: Feb. 17, 2021

(87) PCT Pub. No.: WO2020/043587
PCT Pub. Date: Mar. 5, 2020

(65) Prior Publication Data
US 2021/0251896 A1  Aug. 19, 2021

Related U.S. Application Data

(60) Provisional application No. 62/723,561, filed on Aug. 28, 2018.

(51) Int. Cl.
| | | |
|---|---|---|
| A61K 9/10 | (2006.01) | |
| A61K 31/167 | (2006.01) | |
| A61K 47/10 | (2017.01) | |
| A61K 47/14 | (2017.01) | |
| A61K 47/18 | (2017.01) | |
| A61K 47/26 | (2006.01) | |
| A61K 47/36 | (2006.01) | |

(52) U.S. Cl.
CPC .............. *A61K 9/10* (2013.01); *A61K 31/167* (2013.01); *A61K 47/10* (2013.01); *A61K 47/14* (2013.01); *A61K 47/183* (2013.01); *A61K 47/26* (2013.01); *A61K 47/36* (2013.01)

(58) Field of Classification Search
None
See application file for complete search history.

(56) References Cited

U.S. PATENT DOCUMENTS

2003/0118654 A1* 6/2003 B. Santos ............ A61K 9/0095
514/192
2006/0093629 A1 5/2006 Buehler
2006/0292214 A1 12/2006 Jenkins et al.

FOREIGN PATENT DOCUMENTS

WO 03/082243 A1 10/2003
WO 04/012708 A1 2/2004

* cited by examiner

*Primary Examiner* — Robert A Wax
*Assistant Examiner* — Quanglong N Truong
(74) *Attorney, Agent, or Firm* — Christopher S. Dodson

(57) ABSTRACT

Pharmaceutical liquid suspensions containing paracetamol wherein the suspensions are formulated with paracetamol particles having a d50 of less than or equal to 10 μm and a d90 of less than or equal to 35 μm such that browning discoloration is reduced during prolonged storage.

19 Claims, 6 Drawing Sheets

First color measurements to compare Formulation A samples (48mg/ml) with Formulation B samples (24 and 48mg/ml) and Formulation C samples (24mg/ml) over a storage time of maximum 6 months (6M) at different temperature conditions

PARACETAMOL LIQUID SUSPENSIONS

This application claims priority under 35 U.S.C. § 371 to International Application No. PCT/EP2019/072445, filed 22 Aug. 2019, which claims the benefit of U.S. Provisional Application No. 62/723,561, filed 28 Aug. 2018, the entireties of which are incorporated by reference herein.

FIELD OF THE INVENTION

The present invention relates to pharmaceutical liquid suspensions suitable for oral administration. More specifically, the present invention relates to pharmaceutical liquid suspensions containing N-acetyl-p-aminophenol, known by the generic names paracetamol, acetaminophen and APAP (hereinafter referred to as paracetamol). In particular, the invention relates to paracetamol liquid suspensions that are formulated with paracetamol particles having a d50 of less than or equal to 10 μm and a d90 of less than or equal to 35 μm such that browning discoloration is reduced during prolonged storage, compared with paracetamol liquid suspensions that are formulated with paracetamol particles having larger average particle sizes.

BACKGROUND OF THE INVENTION

Paracetamol is a commonly used analgesic and antipyretic drug that has been available in many countries for more than 40 years. A wealth of experience clearly establishes it as the standard antipyretic and analgesic for mild to moderate pain states. Paracetamol is available in many countries for non-prescription over-the-counter sale in conventional orally administered dosage forms, including solid forms, such as, capsules, caplets, gel caps, or tablets, and liquid forms, such as, solutions, e.g., syrups and elixirs, emulsions, or suspensions.

Medicaments administered in solid form are usually intended to be swallowed whole. However, children, and some adults, including disabled or incapacitated patients, have trouble swallowing solid dosage forms even if the tablet or capsule is very small. Chewable tablets are an option as well, but are unacceptable if the active pharmaceutical ingredient (API) has a disagreeable taste. For many patients, including pediatric and geriatric patients, a liquid oral dosage form is preferable over chewable dosage form because of the ready swallowability without chewing of the liquid dosage form. Liquid dosage forms can be either syrups or suspensions.

Liquid suspensions are a two-phase system having solid, poorly water-soluble API particles, dispersed throughout liquid medium. In a suspension, the API does not dissolve, or dissolves to a limited extent, in the liquid medium and therefore, remains intact in the form of small particles. A suspension does not encompass emulsions, which are meant to describe liquids suspended within liquid carriers. Nor does a suspension encompass syrup formulations, which contain fully dissolved APIs.

The preparation of such a suspension is often underestimated and involves more than mixing a solid in a liquid. Knowledge of particles behavior in the liquids, as well as wetting agents, suspending agents, polymers, preservatives, colors and flavors is needed in order to manufacture a product with the targeted quality attributes (David B. Troy, Paul Beringer, The Science and Practice of Pharmacy, p. 767-768, Lippincott Williams & Wilkins, 2006).

One challenge associated with liquid suspensions is sedimentation, that is the tendency for particles in suspension to settle out of the fluid. Among all the ingredients of a suspension, the suspended phase (i.e., containing API particles, in this case, paracetamol particles) is one of the most critical components since it might tend to sediment over time and under specific conditions. Different factors influence the sedimentation rate of particles in suspension. Stokes' law is often used to express the sedimentation rate:

$$\frac{dS}{dt} = \frac{d^2(\rho_P - \rho_M)g}{18\eta},$$

Where dS/dt is the sedimentation rate, d is the diameter of the particles, $\rho_P$ is the density of the particles, $\rho_M$ is the density of the medium, g is the gravitational constant and η is the viscosity of the medium. According to Stokes' law, the sedimentation rate of a suspension decreases with decreasing the particle diameter; decreasing the difference between particle density and density of the medium; and increasing the viscosity of the medium.

U.S. Pat. Nos. 5,272,137 and 5,409,907 teach the use of suspending agents such as xanthan gum and microcrystalline cellulose to minimize sedimentation. U.S. Pat. No. 5,658,919 discloses the use of xanthan gum, a mixture of microcrystalline cellulose and sodium carboxymethylcellulose, and an auxiliary suspending agent selected from hydroxyethylcellulose and a salt of carboxymethylcellulose to minimize sedimentation of paracetamol suspensions.

Color change in pharmaceutical products, which typically occurs during product storage, is considered an important quality attribute and is often monitored as an indication of non-adequate product manufacture or formulation instability. Color is therefore monitored during pharmaceutical product development. Color change in pharmaceutical products can occur under specific conditions. The color of a paracetamol-containing liquid formulation can change more easily than a paracetamol-containing solid formulation, since color change might be caused by several reactions such as paracetamol degradation through hydrolysis reactions or oxidation reactions; and other chemical reactions of active ingredients and other additives, e.g., Maillard reactions.

Color change in a paracetamol suspension usually occurs as discoloration from white to off-white or brown. For this reason, color change is often described with the terms discoloration or browning. Dyes are often added to pharmaceutical suspensions for improved appearance and patient acceptability, and to mask discoloration. However, it has been found that some patients develop or have allergies to or are sensitive to dyed suspension or that such suspensions stain clothing, furniture, carpeting, and the like when spilled. Therefore, dye-free suspensions are very desirable. Coloring agents are often added to pharmaceutical liquid products to produce pharmaceutically acceptable characteristics, to provide an identifying factor and also to provide consistency among the batches of a product. Often the color of the excipients that are used to manufacture product contribute an off-color to the product. This color is often dependent on the lots of excipients and they can change on storage with no adverse effect on the product. The consumer would however, perceive the color change as having an adverse effect on the effectiveness of the product, potentially resulting in rejection of the product.

EP 2 229 937 B1 relates to a dye-free paracetamol liquid suspension comprising by gram per 100 mL of the suspension 1 to 15 APAP having an average particle size of between 10 and 100 microns; 0.1 to 0.25 xanthan gum; 0.4 to 1 microcrystalline cellulose; to 65 sorbitol solution; 1 to 20 glycerin; 0.01 to 1 flavoring; 20 to 50 water; 0.001 to 0.10 of an antimicrobial preservative selected from the group consisting of butylparaben, methylparaben, propylparaben, and combinations thereof; 0.003 to 0.20 citric acid; and 0.1 to 0.5 propylene glycol; wherein the dye-free APAP suspension has a pH of from 5 to 6 and is substantially free of a reducing sugar. The formulation contains sucrose. According to EP 2 229 937 B1, the unique combination of APAP having sorbitol and sucrose at a pH from about 5.1 to 5.9 produces advantageously storage stable and homogeneously dispersed suspensions of APAP.

U.S. Pat. No. 7,300,670 teaches a suspension containing one particulate drug with a density of from about 0.9 to about 1.6 g/ml, an average particle size (×50) of less than about 20 microns, a polymer exhibiting plastic flow selected from but not limited to xanthan gum, carbomer, microcrystalline cellulose, carboxymethyl-cellulose, sodium carboxymethylcellulose, and combinations thereof, and wherein the suspension has a final yield value of less than about 15 Pa, to ensure that the product is pourable without shaking, and which does not cake on storage and which is able to maintain its homogeneity on prolonged storage without shaking. The Examples in the '670 patent teach from 0.02 to 15 percent by weight acetaminophen liquid suspensions containing invert sugars, sucrose and colorants or dyes.

Despite the challenges associated with formulating suspensions many attempts have been made to formulate paracetamol as a liquid suspension. Indeed, there are numerous products currently on the market, including Panadol® Children's 1-6 Years (sold by GlaxoSmithKline Consumer Healthcare), Children's Tylenol Pain and Fever Reliever (sold by Johnson & Johnson Consumer Inc.) and Panodil Jr. suspension.

The present invention is an improvement over these commercial products and relates to the discovery of a dye-free, optionally sugar-free, storage stable paracetamol liquid suspension that provides an organoleptically pleasing mouth feel, low sedimentation and a surprisingly advantageous reduction in browning over a prolonged time period.

SUMMARY OF THE INVENTION

The present invention is directed to a pharmaceutical composition comprising paracetamol particles having a d50 of less than or equal to 10 μm and a d90 of less than or equal to 35 μm, which composition is substantially dye-free.

In another embodiment, the invention is directed to a pharmaceutical composition comprising paracetamol particles having a d50 of less than or equal to 10 μm and a d90 of less than or equal to 30 μm, which composition is substantially dye-free.

In a further embodiment, the invention is directed to a pharmaceutical composition comprising paracetamol particles having a d50 of less than or equal to 10 μm and a d90 of less than or equal to 25 μm, which composition is substantially dye-free.

In still another embodiment, the invention is directed to a pharmaceutical composition comprising paracetamol particles having a d50 of less than or equal to 10 μm and a d90 of less than or equal to 20 μm, which composition is substantially dye-free.

In yet another embodiment, the invention is directed to a pharmaceutical composition comprising paracetamol particles having a d50 of less than or equal to 10 μm and a d90 of less than or equal to 16 μm, which composition is substantially dye-free.

In still yet another embodiment, the invention is directed to a pharmaceutical composition comprising paracetamol particles having a d50 of less than or equal to 8 μm and a d90 of less than or equal to 35 μm, which composition is substantially dye-free.

In another embodiment, the invention is directed to a pharmaceutical composition comprising paracetamol particles having a d50 of less than or equal to 8 μm and a d90 of less than or equal to 30 μm, which composition is substantially dye-free.

In a further embodiment, the invention is directed to a pharmaceutical composition comprising paracetamol particles having a d50 of less than or equal to 8 μm and a d90 of less than or equal to 25 μm, which composition is substantially dye-free.

In another embodiment, the invention is directed to a pharmaceutical composition comprising paracetamol particles having a d50 of less than or equal to 8 μm and a d90 of less than or equal to 20 μm, which composition is substantially dye-free.

In yet another embodiment, the invention is directed to a pharmaceutical composition comprising paracetamol particles having a d50 of less than or equal to 8 μm and a d90 of less than or equal to 16 μm, which composition is substantially dye-free.

In one embodiment, the invention is directed to a pharmaceutical composition comprising paracetamol particles having a d50 of less than or equal to 10 μm and a d90 of less than or equal to 35 μm, which composition is substantially dye-free and is substantially free of invert sugars.

In another embodiment, the invention is directed to a pharmaceutical composition comprising paracetamol particles having a d50 of less than or equal to 10 μm and a d90 of less than or equal to 30 μm, which composition is substantially dye-free and is substantially free of invert sugars.

In a further embodiment, the invention is directed to a pharmaceutical composition comprising paracetamol particles having a d50 of less than or equal to 10 μm and a d90 of less than or equal to 25 μm, which composition is substantially dye-free and is substantially free of invert sugars.

In yet a further embodiment, the invention is directed to a pharmaceutical composition comprising paracetamol particles having a d50 of less than or equal to 10 μm and a d90 of less than or equal to 20 μm, which composition is substantially dye-free and is substantially free of invert sugars.

In still yet a further embodiment, the invention is directed to a pharmaceutical composition comprising paracetamol particles having a d50 of less than or equal to 10 μm and a d90 of less than or equal to 16 μm, which composition is substantially dye-free and is substantially free of invert sugars.

In one embodiment, the invention is directed to a pharmaceutical composition comprising paracetamol particles having a d50 of less than or equal to 8 μm and a d90 of less than or equal to 35 μm, which composition is substantially dye-free and is substantially free of invert sugars.

In another embodiment, the invention is directed to a pharmaceutical composition comprising paracetamol particles having a d50 of less than or equal to 8 μm and a d90 of less than or equal to 30 μm, which composition is substantially dye-free and is substantially free of invert sugars.

In a further embodiment, the invention is directed to a pharmaceutical composition comprising paracetamol particles having a d50 of less than or equal to 8 μm and a d90 of less than or equal to 25 μm, which composition is substantially dye-free and is substantially free of invert sugars.

In yet a further embodiment, the invention is directed to a pharmaceutical composition comprising paracetamol particles having a d50 of less than or equal to 8 μm and a d90 of less than or equal to 20 μm, which composition is substantially dye-free and is substantially free of invert sugars.

In still yet a further embodiment, the invention is directed to a pharmaceutical composition comprising paracetamol particles having a d50 of less than or equal to 8 μm and a d90 of less than or equal to 16 μm, which composition is substantially dye-free and is substantially free of invert sugars.

In one embodiment, the invention is directed to a pharmaceutical composition comprising paracetamol particles with a d50 of less than or equal to 10 μm and a d90 of less than or equal to 35 μm, which composition is substantially dye-free and is substantially free of reducing sugars.

In another embodiment, the invention is directed to a pharmaceutical composition comprising paracetamol particles with a d50 of less than or equal to 10 μm and a d90 of less than or equal to 30 μm, which composition is substantially dye-free and is substantially free of reducing sugars.

In a further embodiment, the invention is directed to a pharmaceutical composition comprising paracetamol particles with a d50 of less than or equal to 10 μm and a d90 of less than or equal to 25 μm, which composition is substantially dye-free and is substantially free of reducing sugars.

In yet a further embodiment, the invention is directed to a pharmaceutical composition comprising paracetamol particles with a d50 of less than or equal to 10 μm and a d90 of less than or equal to 20 μm, which composition is substantially dye-free and is substantially free of reducing sugars.

In still yet a further embodiment, the invention is directed to a pharmaceutical composition comprising paracetamol particles with a d50 of less than or equal to 10 μm and a d90 of less than or equal to 16 μm, which composition is substantially dye-free and is substantially free of reducing sugars.

In one embodiment, the invention is directed to a pharmaceutical composition comprising paracetamol particles with a d50 of less than or equal to 8 μm and a d90 of less than or equal to 35 μm, which composition is substantially dye-free and is substantially free of reducing sugars.

In another embodiment, the invention is directed to a pharmaceutical composition comprising paracetamol particles with a d50 of less than or equal to 8 μm and a d90 of less than or equal to 30 μm, which composition is substantially dye-free and is substantially free of reducing sugars.

In a further embodiment, the invention is directed to a pharmaceutical composition comprising paracetamol particles with a d50 of less than or equal to 8 μm and a d90 of less than or equal to 25 μm, which composition is substantially dye-free and is substantially free of reducing sugars.

In yet a further embodiment, the invention is directed to a pharmaceutical composition comprising paracetamol particles with a d50 of less than or equal to 8 μm and a d90 of less than or equal to 20 μm, which composition is substantially dye-free and is substantially free of reducing sugars.

In still yet a further embodiment, the invention is directed to a pharmaceutical composition comprising paracetamol particles with a d50 of less than or equal to 8 μm and a d90 of less than or equal to 16 μm, which composition is substantially dye-free and is substantially free of reducing sugars.

In one embodiment, the invention is directed to a pharmaceutical composition comprising paracetamol particles with a d50 of less than or equal to 10 μm and a d90 of less than or equal to 35 μm, which composition is substantially dye-free and is substantially free of reducing sugars and substantially free of invert sugars.

In another embodiment, the invention is directed to a pharmaceutical composition comprising paracetamol particles with a d50 of less than or equal to 10 μm and a d90 of less than or equal to 30 μm, which composition is substantially dye-free and is substantially free of reducing sugars and substantially free of invert sugars.

In a further embodiment, the invention is directed to a pharmaceutical composition comprising paracetamol particles with a d50 of less than or equal to 10 μm and a d90 of less than or equal to 25 μm, which composition is substantially dye-free and is substantially free of reducing sugars and substantially free of invert sugars.

In yet a further embodiment, the invention is directed to a pharmaceutical composition comprising paracetamol particles with a d50 of less than or equal to 10 μm and a d90 of less than or equal to 20 μm, which composition is substantially dye-free and is substantially free of reducing sugars and substantially free of invert sugars.

In still yet a further embodiment, the invention is directed to a pharmaceutical composition comprising paracetamol particles with a d50 of less than or equal to 10 μm and a d90 of less than or equal to 16 μm, which composition is substantially dye-free and is substantially free of reducing sugars and substantially free of invert sugars.

In one embodiment, the invention is directed to a pharmaceutical composition comprising paracetamol particles with a d50 of less than or equal to 8 μm and a d90 of less than or equal to 35 μm, which composition is substantially dye-free and is substantially free of reducing sugars and substantially free of invert sugars.

In another embodiment, the invention is directed to a pharmaceutical composition comprising paracetamol particles with a d50 of less than or equal to 8 μm and a d90 of less than or equal to 30 μm, which composition is substantially dye-free and is substantially free of reducing sugars and substantially free of invert sugars.

In a further embodiment, the invention is directed to a pharmaceutical composition comprising paracetamol particles with a d50 of less than or equal to 8 μm and a d90 of less than or equal to 25 μm, which composition is substantially dye-free and is substantially free of reducing sugars and substantially free of invert sugars.

In yet a further embodiment, the invention is directed to a pharmaceutical composition comprising paracetamol particles with a d50 of less than or equal to 8 μm and a d90 of less than or equal to 20 μm, which composition is substantially dye-free and is substantially free of reducing sugars and substantially free of invert sugars.

In still yet a further embodiment, the invention is directed to a pharmaceutical composition comprising paracetamol particles with a d50 of less than or equal to 8 μm and a d90 of less than or equal to 16 μm, which composition is substantially dye-free and is substantially free of reducing sugars and substantially free of invert sugars.

In one embodiment a composition according to the invention is substantially free of a non-reducing sugar which is sucrose.

DETAILED DESCRIPTION OF THE INVENTION

Definitions

As used herein, the term 'invert sugar' is a mixture of glucose and fructose obtained by the hydrolysis of sucrose. In sucrose, the enzyme invertase, yields "invert sugar" (so called because the hydrolysis results in an inversion of the rotation of plane polarized light), a 50:50 mixture of fructose and glucose, its two constituent monosaccharides. It will be understood that the terms "substantially free of an invert sugar" or "substantially free of invert sugars" means that an invert sugar is not added as a separate component to the formulations described herein at any point during their manufacture and therefore, is not a separate component of the end-product liquid suspension. It will be understood that trace amounts of invert sugars may be found in one or more of the excipients used in the formulation, e.g., as may be found in polyols such as maltitol and sorbitol.

As used herein, a "particle" may be a crystal, a granule, an agglomerate, or any undissolved solid material.

As used herein, the term "prolonged period of time" means a time frame that is greater than about 12 months. In one embodiment, the prolonged period of time is up to and including about 18 months. In another embodiment, the prolonged period of time is up to and including about 24 months. In a further embodiment, the prolonged period of time is up to and including about 36 months. As used herein, the term "reducing sugar" is any sugar that can act as a reducing agent (and thus can be oxidized) because it has a free aldehyde group or a free ketone group. All monosaccharides are reducing sugars, along with some disaccharides, oligosaccharides, and polysaccharides. The monosaccharides can be divided into two groups: the aldoses, which have an aldehyde group, and the ketoses, which have a ketone group. Ketoses must first tautomerize to aldoses before they can act as reducing sugars. The common dietary monosaccharides galactose, glucose and fructose are all reducing sugars. It will be understood that sucrose is made up of two monosaccharides—glucose and fructose. Since the reducing groups of glucose and fructose (i.e., the free aldehyde/ketone groups) are involved in glycosidic bond formation and are not available, sucrose is a non-reducing sugar As used herein, the term "substantially dye-free" means that at a dye is not added as a separate component to the formulations described herein at any point during their manufacture and therefore, is not a separate component of the end-product pharmaceutical liquid suspension.

It will be understood that the terms "substantially free of a reducing sugar" or "substantially free of reducing sugars" means that a reducing sugar is not added as a separate component to the formulations described herein at any point during their manufacture and therefore, is not a separate component of the end-product pharmaceutical liquid suspension. It will be further understood that trace amounts of reducing sugars may be found in one or more of the excipients used in the formulation, e.g., in the maltitol syrup or the sorbitol solution. Based on a certificate of analysis for maltitol syrup, there is less than 0.10% of reducing sugars, on a dry basis (commercially available from Roquette Freres, France). Based on a certificate of analysis for sorbitol 70% solution, there is for example 0.08% of reducing sugars, on a dry basis; for a maximum of 0.14% of reducing sugars (commercially available from Roquette Freres, France).

It will be understood that the term "substantially free of a non-reducing sugar which is sucrose" means that sucrose is not added as a separate component to the formulations described herein at any point during their manufacture and therefore, is not a separate component of the end-product pharmaceutical liquid suspension.

The active agent or ingredient is present in a "unit dose volume" of the aqueous suspension in a therapeutically effective amount, which is an amount that produces the desired therapeutic response upon oral administration and can be readily determined by one skilled in the art. In determining such amounts, the active agent being administered, the bioavailability characteristics of the active agent, the dose regime, the age and weight of the patient, and other factors must be considered, as known in the art. As used herein a "unit dose volume" of the aqueous suspension is a convenient volume for dosing the product to a patient. The dosing directions instruct the patient to take amounts that are multiples of the unit dose volume depending on, e.g., the age or weight of the patient. Typically, the unit dose volume of the suspension will contain an amount of active agent that is therapeutically effective for the smallest patient. For example, suitable unit dose volumes may include one teaspoonful (about 5 mL), one tablespoonful (about 15 mL), one dropperful, or one milliliter.

BRIEF DESCRIPTION OF THE FIGURES

Paracetamol can be affected by multiple degradation reactions. This is a particular concern when formulating paracetamol as a pharmaceutical liquid suspension. FIG. 1 shows the degradation products of paracetamol in solution. According to the reaction mechanisms in FIG. 1, paracetamol hydrolyzes in aqueous solution to form p-aminophenol which then oxidizes further to form pink-colored quinine imines. The influence of oxygen on discoloration of a paracetamol solution is a consequence of both oxygen in the bottle head space of the container and oxygen dissolved in the liquid. Recommendations given to limit discoloration are to: (a) manage the amount of oxygen in the container by controlling filling volume and headspace; (b) ensure appropriate packaging selection to minimize oxygen transfer through the packaging; (c) use a de-aeration method under reduced pressure or replace oxygen with an inactive gas (e.g., nitrogen) during manufacturing and/or filling; (d) consider the use of antioxidants in the formulation in order to minimize oxidation; and (e) remove or replace excipients or primary packaging components that could promote oxidation, such as trace metal ions, hydroperoxides or residual initiators in polymers. (Mochizuchi, K et al., *Prediction of color changes in acetaminophen solution using the time-temperature superposition principle*, Drug Development and Industrial Pharmacy, Vol. 42, No. 7, 1050-1057, (2015)).

Figure 1:
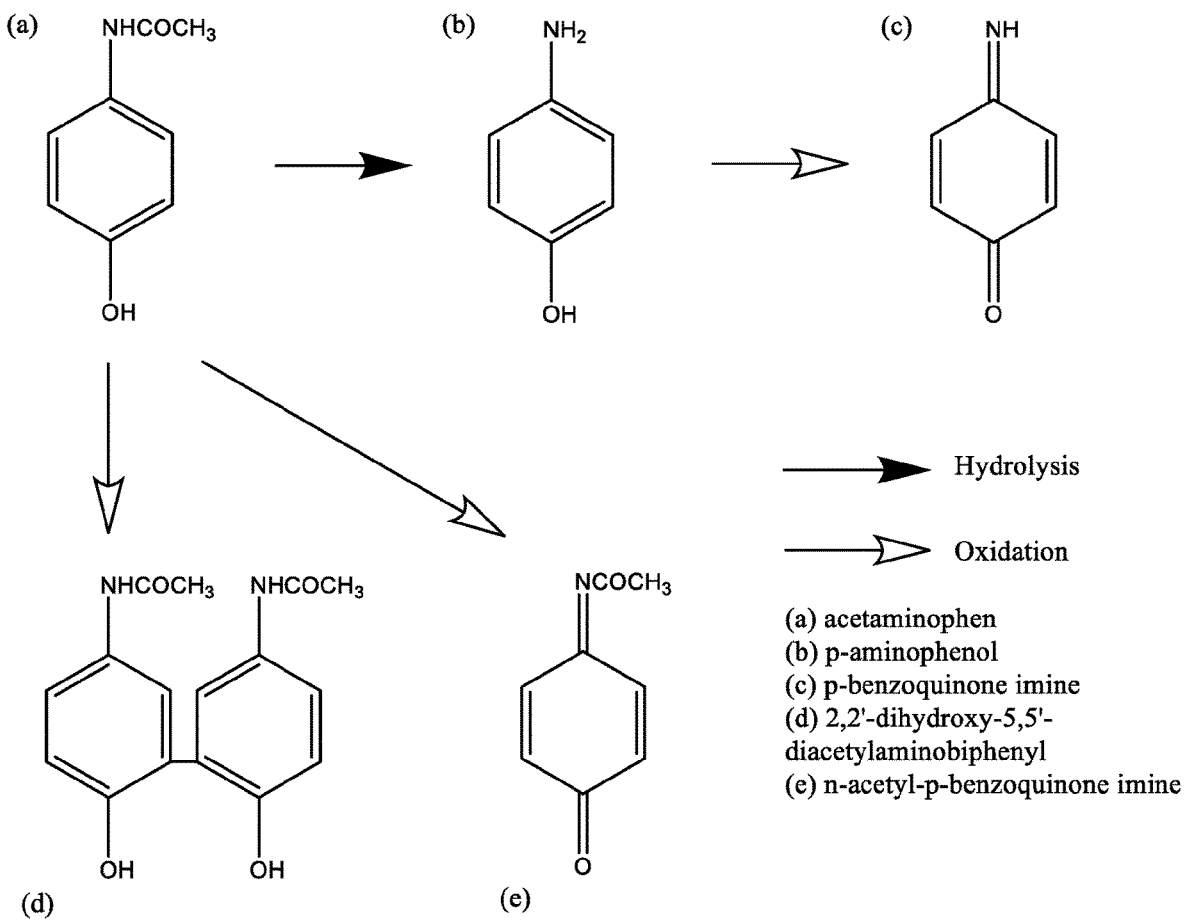
FIG. 1 depicts degradation products of paracetamol in solution. Koshy K. T., Lach J. L. (1961). Stability of aqueous solutions of N-acetyl-paminophenol. J Pharm Sci 50:113-18. Imaizumi H, Nagai K (1978). Stability of non-pyrine antipyretic analgesic. J. Pract. Pharm. 29:1161-6.

There is no recognition in the literature that reducing the particle size of the paracetamol particles could be a factor in limiting discoloration in a paracetamol-containing pharmaceutical liquid suspension. Furthermore, there is no recognition that a paracetamol pharmaceutical liquid suspension formulated with paracetamol particles having a d50 of less than or equal to 10 μm and a d90 of less than or equal to 35 μm would significantly limit discoloration such that the formulation can be substantially dye-free, and still present a commercially acceptable product.

It has also been found that temperature has an important impact on the hydrolysis reaction rate of paracetamol and therefore browning, since a temperature increase translates into an increase of paracetamol solubility i.e., concentration in solution (Koshy K. T. et al., (1961), Stability of aqueous solutions of N-acetyl-paminophenol, *J Pharm Sci* 50:113-18 and Imaizumi H et al., (1978). Stability of non-pyrine antipyretic analgesic, *J Pract. Pharm,* 29:1161-6).

Sedimentation is also a challenge when formulating liquid suspensions. The viscosity of the suspension is known to have an impact on sedimentation. In general, as the viscosity increases, the sedimentation rate decreases.

The particle size of the API is also generally thought to affect the sedimentation rate of a suspension. The larger the particle size, one would expect the sedimentation rate to increase. As the particle size decreases, one would expect the sedimentation rate to decrease. However, as the particle size decreases, one would also expect the color of the suspension to be negatively affected, i.e., an increase in browning is expected because the surface area of the particles is larger and therefore there is more surface exposure to degradation reactions.

Surprisingly, the opposite was found by the inventors herein. The invention relates to a paracetamol pharmaceutical liquid suspension wherein the particle size distribution (d50 and d90) and the particle size span is significantly smaller than that found in commercial products. Despite the smaller particle size distribution, the invention provides a storage stable suspension that does not brown over a prolonged time period and, therefore, does not require a dye to mask discoloration or browning.

One of the most widely used methods of describing particle size distributions are percentiles or "d" values. The d10, d50 and d90 values are particle size values corresponding to the cumulative distribution at 10%, 50% and 90%. Based on a mass distribution, a d-value can be thought of as a "mass division diameter". It is the diameter which, when all particles in a sample are arranged in order of ascending mass, divides the sample's mass into specified percentages. The percentage mass below the diameter of interest is the number expressed after the "d". For example, the d10 diameter is the diameter at which 10% of a sample's mass is comprised of smaller particles, and the d50 is the diameter at which 50% of a sample's mass is comprised of smaller particles. The d50 is also known as the "mass median diameter" as it divides the sample equally by mass.

Median values are defined as the value where half of the population of particles of a specified size resides above the median point, and half of the population of particles of a specified size resides below the median point. For particle size distributions, the median is called the d50 (or ×50 when following certain International Organization of Standardization guidelines). The d50 is the size in microns that splits the particle population distribution with half above and half below a certain diameter size. For example, according to this invention, a paracetamol particle size distribution defined as a d50 of 10 μm means that 50% of the paracetamol particles are smaller than 10 μm and 50% of the paracetamol particles are larger than 10 μm. For further details see, page 4, https://www.horiba.com/fileadmin/uploads/Scientific/eMag/PSA/Guidebook/pdf/PSA_Guidebook.pdf.

As defined herein, the span or width of the particle size distribution is defined as follows:

$$SPAN = \frac{d90 - d10}{d50}$$

It will be understood that the lower the span, the narrower a particle size distribution is. Suitably the paracetamol particles of use in the invention have a span that is less than 4.5, for example from about 0.1 to about 4 or from about 0.5 to about 3.5. In one embodiment the span is from about 1 to about 3. In one embodiment the span is from about 2 to about 3. In the present invention a good approximation of the span equation above is the d90/d50 value, given that the d10 value is much smaller than d90. Clearly with d50 values so low, and d10, by definition, even lower, the d10 parameter will not materially affect the span. Suitably in one aspect according to the invention, the paracetamol particles have a d10 value that is less than about 5 μm for example less than about 4 μm or less than about 3 μm. In one embodiment the paracetamol particles have a d10 value that is about 2 μm.

The typical percentile values for paracetamol particle size distribution as used herein, was measured by a laser diffraction particle size analyzer (Malvern, Mastersizer 2000) and d values are based on a volume distribution.

The present invention is related to the discovery that when the particle size distribution of paracetamol in a pharmaceutical liquid suspension and the span of the particle size distribution of paracetamol in a pharmaceutical liquid suspension is specifically defined, the browning of the suspension is significantly reduced over a prolonged period of time.

Suitably, the paracetamol particles have a d50 of less than or equal to 10 μm. In one embodiment, the paracetamol particles have a d50 from 5 μm to 10 μm. In another embodiment, the paracetamol particles have a d50 from 8 μm to 10 μm. In a further embodiment, the paracetamol particles have a d50 less than or equal to 8 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is less than or equal to 10 μm and the d90 is less than or equal to 35 μm. In another embodiment, the paracetamol particles have a distribution range wherein the d50 is less than or equal to 10 μm and the d90 is less than or equal to 30 μm. In a further embodiment, the paracetamol particles have a distribution range wherein the d50 is less than or equal to 10 μm and the d90 is less than or equal to 25 μm. In yet another embodiment, the paracetamol particles have a distribution range wherein the d50 is less than or equal to 10 μm and the d90 is less than or equal to 20 μm. In still yet another embodiment, the paracetamol particles have a distribution range wherein the d50 is less than or equal to 10 μm and the d90 is less than or equal to 16 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is from 5 μm to 10 μm and the d90 is less than or equal to 35 μm. In one embodiment, the paracetamol particles have a distribution range wherein the d50 is from 8 μm to 10 μm and the d90 is less than or equal to 35 μm. In another embodiment, the paracetamol particles have a distribution range wherein the d50 is less than or equal to 8 μm and the d90 is less than or equal to 35 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is from 5 μm to 10 μm and the d90 is less than or equal to 30 μm. In one embodiment, the paracetamol particles have a distribution range wherein the d50 is from 8 μm to 10 μm and the d90 is less than or equal to 30 μm. In another embodiment, the paracetamol particles have a distribution range wherein the d50 is less than or equal to or equal to 8 μm and the d90 is less than or equal to 30 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is from 5 μm to 10 μm and the d90 is less than or equal to 25 μm. In one embodiment, the paracetamol particles have a distribution range wherein the d50 is from 8 μm to 10 μm and the d90 is less than or equal to 25 μm. In another embodiment, the paracetamol particles have a distribution range wherein the d50 is less than or equal to 8 μm and the d90 is less than or equal to 25 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is from 5 μm to 10 μm and the d90 is less than or equal to 20 μm. In one embodiment, the paracetamol particles have a distribution range wherein the d50 is from 8 μm to 10 μm and the d90 is less than or equal to 20 μm. In another embodiment, the paracetamol particles have a distribution range wherein the d50 is less than or equal to 8 μm and the d90 is less than or equal to 20 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Suitably, the paracetamol particles have a distribution range wherein the d50 is from 5 μm to 10 μm and the d90 is less than or equal to 16 μm. In one embodiment, the paracetamol particles have a distribution range wherein the d50 is from 8 μm to 10 μm and the d90 is less than or equal to 16 μm. In another embodiment, the paracetamol particles have a distribution range wherein the d50 is less than or equal to 8 μm and the d90 is less than or equal to 16 μm. Suitably, for any of these embodiments, the formulation is substantially dye-free. Suitably, for any of these embodiments, the formulation is substantially dye-free and substantially free of reducing sugars. Suitably, for any of these embodiments, the formulation is substantially dye-free, substantially free of reducing sugars and substantially free of invert sugars.

Paracetamol is present in the instant pharmaceutical liquid suspension in a concentration of from about 2.0 to about 5.0% weight/volume (it will be understood by the skilled artisan that 2.0% weight/volume is equivalent to 2.0 grams/100 mL of suspension which is equivalent to 20 milligrams/mL of suspension). In one embodiment of the invention, paracetamol is present in an amount of 2.4 grams/100 mL suspension. In another embodiment of the invention, paracetamol is present in an amount of 3.2 grams/100 mL of suspension. In a further embodiment of the invention, paracetamol is present in an amount of 4.8 grams/100 mL of suspension.

Water is present in the pharmaceutical liquid suspension according to the invention. Suitably water is present in an amount of from about 30 to about 70% weight/volume (it will be understood that 70% is equivalent to 70 grams per 100 mL of suspension. In one embodiment of the invention, water is present in an amount of about 40 to about 60% weight/volume such as about 50% i.e. about 50 grams per 100 mL. It will be understood that the amount of water includes both free water added and water added with other materials such as with sorbitol and/or maltitol solutions.

The pharmaceutical liquid suspension of the invention may contain additional ingredients known to one of skill in the art, generally referred to as additives. Additives can include, but are not limited to, known components such as flavoring agents, sweeteners, antioxidants, chelating agents, thickeners, preservatives, pH modifiers, surfactants, antifoaming agents, co-solvents, humectants, and mixtures thereof.

Water-soluble high intensity sweeteners also may be employed in this invention. Examples of suitable high intensity sweeteners include, but are not limited to, sucralose, aspartame, saccharin, acesulfame, cyclamate, and pharmaceutically acceptable salts and combinations thereof. The amount of high intensity sweetener used in the suspension will vary depending on the degree of sweetening desired for the particular suspension. Generally, the amount of high intensity sweeteners used in the suspension may vary from about 0 to about 2.0 grams per 100 mL of suspension. In embodiments employing a high intensity sweetener, such as sucralose, aspartame, acesulfame, saccharin, and pharmaceutically acceptable salts thereof, the level of high intensity sweetener is from about 0 to about 1 gram per 100 mL of suspension. In one embodiment the high intensity sweetener is sucralose. In one embodiment of the invention, the suspension comprises a high intensity sweetener at about 0 to about 0.5 gram per 100 mL of suspension for example from about 0.1 to about 0.4 grams per 100 mL of suspension.

Suitably, polyhydric alcohols for use as sweeteners in the present invention include, but are not limited to, sorbitol, mannitol, xylitol, erythritol, maltitol, and the like, and combinations thereof. The amount of polyhydric alcohol sweetener used in the suspension will vary depending on the degree of sweetening desired for the particular suspension. Generally, the amount of polyhydric alcohol sweetener may be in the range of from about 0 to about 90 grams per 100 mL of the suspension. In the present invention, the suspension comprises maltitol solution at about 20 to about 70 grams per 100 mL of the suspension. In one embodiment, the suspension comprises maltitol solution at about 50 to about 70 grams per 100 mL of the suspension. In another embodiment, the suspension comprises maltitol solution at about 50 to about 60 grams per 100 mL of the suspension. In one embodiment, the suspension comprises sorbitol solution (as a 70% aqueous solution) at about 0 to about grams per 100 mL of the suspension. In another embodiment, the suspension comprises sorbitol solution (as a 70% aqueous solution) at about 5 to about 15 grams per 100 mL of the suspension. In another embodiment, the suspension comprises sorbitol solution (as a 70% aqueous solution) at about 10 to about 15 grams per 100 mL of the suspension. In one embodiment the suspension comprises a sorbitol solution (as a 70% aqueous solution) at about 10 to about 20 grams per 100 mL of the suspension and a maltitol solution at about 50 to about 60 grams per 100 mL of the suspension. Suitably the sorbitol solution is a non-crystallizing sorbitol solution.

Suitable flavoring agents include natural and/or artificial flavors such as mint (i.e., peppermint, spearmint, etc.), menthol, cinnamon, vanilla, artificial vanilla, chocolate, artificial chocolate, both natural and/or artificial fruit flavors (e.g., cherry, grape, orange, strawberry, and the like) and combinations of two or more thereof. Flavoring agents are often complex mixtures of chemical compounds dissolved or dispersed in an inert medium, such as, propylene glycol. These solutions or dispersions are generally provided as a minor component of the suspension in amounts effective to provide a palatable flavor to the suspension. In one embodiment, flavoring agents are present in the suspension in amounts in the range of from 0.01 to 1 grams per 100 mL of the suspension. In one embodiment, flavoring agents are present in the suspension in amounts in the range of from 0.05 to 0.15 grams per 100 mL of the suspension.

The pH of the suspension should be optimized to minimize the solubility and maximize the chemical stability of the unpleasant tasting and hydrolysis susceptible active agent, APAP. In the present invention, the pH of the suspension is suitably in the range from 4.5 to 6 or from 5.5 to 6.5. In one embodiment of the invention, the pH of the suspension is 4.7-5.5. In one embodiment the pH of the suspension about 6.0. Suitably, in one embodiment the target pH of a suspension according to the invention is about 5.0.

The suspension can be buffered using pH adjusting agents to maintain the pH of the suspension in the desired pH range. Suitable pH-adjusting agents may be present in the suspension in amounts sufficient to provide the desired degree of pH buffering. The pH-adjusting agents are typically used in the range of from about 0 to about 1 gram per 100 mL of the dye-free pharmaceutical suspension. The pH adjusting agent may be selected from weak organic acids, such as, citric acid, malic acid, sodium citrate (dihydrate), glutamic acid, and the like having acceptable taste characteristics for use in taste-masked oral suspensions. In the present invention, citric acid is present at 0.003 to 0.20 grams per 100 mL of suspension. Citric acid is added to the suspension to stabilize the pH of the suspension at between 4.5 and 6, e.g., from about 4.7 to about 5.5. Antimicrobial preservatives are selected for their activity within this pH range.

In dye-free suspensions of the present invention, there is optionally an antimicrobial preservative. Suitable preservatives include, but are not limited to, methyl paraben, propyl paraben, sodium methyl paraben, sodium ethyl paraben, sodium propyl paraben and the like and combinations thereof. A combination of sodium methyl, sodium ethyl and sodium propyl parabens may be used, available commercially in one form as Niasept sodium from Clariant. Suitably, the preservatives are present in a percent weight/volume amount of about 0.00 to 0.25 gram per 100 mL of suspension. In one embodiment, the methyl paraben is present in an amount of 0.2 grams/100 mL of suspension. In one embodiment, the propyl paraben is present in an amount of 0.045 grams/100 mL of suspension. In yet another embodiment of the invention, methyl paraben is present in an amount of 0.2 grams/100 mL of suspension and propyl paraben is present in an amount of 0.045 grams/100 mL of suspension.

Suitable chelating agents include, but are not limited to ethylenediaminetetraacetic acid including salts thereof such as the disodium salt and the calcium disodium salt. Suitably the chelating agents are used in a percent weight/volume amount of about 0.005 to 0.015 gram per 100 mL of suspension.

The dye-free pharmaceutical liquid suspension of the present invention is substantially free of coloring agents, such as, dyes, lakes, and the like. However, the dye-free pharmaceutical liquid suspension of the present invention may optionally incorporate certain pigments, e.g., titanium dioxide and the like, as opacifiers.

The suspensions of the present invention can employ suspending systems as known in the art that include, but are not limited to, at least one thickening component. In one embodiment of the invention, the thickening component is present in the pharmaceutical liquid suspension in an amount of about 0.05 to about 1.5 grams per 100 mL of suspension for example from about 0.05 to about 0.70 grams per 100 mL of suspension. In another embodiment of the invention, the thickening component is xanthan gum. In yet another embodiment of the invention, the xanthan gum is present in the pharmaceutical liquid suspension in an amount of about 0.65 grams per 100 mL of suspension.

Another optional component of the pharmaceutical liquid suspensions of the invention a humectant. Suitable humectants for use in the invention include glycerine, sorbitol, polyethylene glycol, propylene glycol, and other edible polyhydric alcohols. Generally, the amount of humectant may be in the range of about 10 to about 20 grams/100 mL of the suspension. In one embodiment of the invention, the humectant is glycerine. In another embodiment of the invention, the humectant is glycerine in the amount of about 10 to about 20 grams such as about 15 grams/100 mL of the suspension.

An exemplary composition according to the invention is a pharmaceutical liquid suspension comprising by grams per 100 mL of the suspension:

(a) a therapeutically effective amount of paracetamol in particulate form wherein the paracetamol particles have a D50 of less than or equal to 10 of less than or equal to 10 µm and a D90 of less than or equal to 20 µm;

(b) about 0.20 to about 0.30 of a high intensity sweetener such as sucralose;

(c) about 40 to about 80 of a polyhydric alcohol sweetener such as a combination of maltitol and sorbitol;

(d) about 0.1 to about 0.3 of a preservative such as a combination of methyl parabens and propyl parabens;

(e) about 0.2 to about 0.4 of a buffering agent;

(f) about 0.5 to about 1 of a thickening agent such as xanthan gum;

(g) about 10 to about 20 of a humectant such as glycerine;

(h) about 0.05 to about 0.1 of a flavouring agent;

(i) about 40 to 60 of water;

and wherein the pH of the composition is about 5.5 to about 6.5.

A suitable process for preparing a suspension composition as described herein is a standard process understood by those of skill in the art, and includes the following steps:

a) transferring polyhydric alcohol sweeteners into a main mixing vessel and adding purified water, and mixing continuously to produce a uniform mixture;

b) dissolving preservatives, if present in the liquid suspension, in purified water in a small pre-mixing vessel while stirring continuously and transferring to the main mixing vessel while stirring continuously;

c) dissolving water soluble ingredients in a small pre-mixing vessel and transferring to the main mixing vessel while stirring continuously;

d) adding thickeners to the main mixing vessel and mixing continuously until a uniform suspension is obtained;

e) adding paracetamol to the main mixing vessel and stirring until a uniform suspension is obtained;

f) adding flavour to the main mixing vessel while stirring continuously; and g) adding and mixing sufficient water to the mixture of step (f) to produce a pharmaceutical suspension in accordance with the invention of 100% desired volume, after which the suspension is transferred to a storage tank before filling, labelling and packaging.

EXAMPLES

The invention will now be illustrated by examples. The examples are not intended to be limiting of the scope of the present invention but read in conjunction with the detailed and general description above, provide further understanding of the present invention and an outline of a preferred composition of the invention. The examples were conducted using three paracetamol pharmaceutical liquid suspensions with the compositions shown in Table 1, below. It will be understood that the units below are in percent weight/ volume, which is grams/100 mL solution.

TABLE 1

| Ingredient | Formulation A | Formulation B | Formulation C |
|---|---|---|---|
| Paracetamol, Ph. Eur. (*) | 2.0-5.0% wt/v (2.0 to 5.0 mg/100 mL; 20 mg/mL to 50 mg/mL) | 2.0-5.0% wt/v (2.0 mg/100 mL; 20 mg/mL to 50 mg/mL) | 2.0-5.0% wt/v (2.0 to 5.0 mg/100 mL; 20 mg/mL to 50 mg/mL) |
| Carbomer, Ph. Eur. | — | 0.20-0.70 | — |
| Xanthan gum, Ph. Eur. | 0.50-1.00 | 0.01-0.08 | 0.50-1.00 |
| Nipasept Sodium | — | 0.10-0.20 | — |
| Methyl Paraben | 0.01 to 0.20 | — | — |
| Propyl Paraben | 0.01 to 0.065 | — | — |
| Sodium Methyl Paraben | — | — | 0.01-0.15 |
| Sodium Ethyl Paraben | — | — | 0.01-0.03 |
| Sodium Propyl Paraben | — | — | 0.01-0.03 |
| Glycerine | 10-20 | — | — |
| EDTA, Ph. Eur. | 0.005-0.015 | 0.005-0.015 | — |
| Non-Crystallizing Sorbitol (70% solution), Ph. Eur. | 10-20 | 10-20 | 10-20 |
| Sorbitol | — | — | 2.0-2.5 |
| Maltitol Solution, Ph. Eur. | 50-60 | 50-60 | 65-75 |
| Malic Acid, Ph. Eur. | — | 0.05-0.15 | 0.01-0.07 |
| Anhydrous citric acid | 0.020-0.030 | — | 0.02 |
| Sodium Citrate (dihydrate) | 0.20-.030 | — | — |
| Sodium Hydroxide, Ph.Eur. | — | 0.10-0.20 | — |
| Sucralose, Ph. Eur. | 0.20-0.30 | 0.05 -.10 | — |
| Acesulfame K, Ph. Eur. | — | 0.01-0.05 | — |
| Strawberry Flavor | 0.05-0.10 | 0.010-0.015 | 0.05-0.15 |
| Orange Flavor | 0.05-0.15 | 0.05-0.15 | — |
| Purified Water | q.s. to 100 | q.s. to 100 | q.s. to 100 |
| pH | 6.0 | 6.0 | 5.0 |

A fine grade of paracetamol (commercially available from Granules India, Ltd. or Farmson Ltd.) was used for Formulation A. A coarser powder grade of paracetamol (commercially available from Granules India, Ltd. or Farmson Ltd.) was used for Formulations B and C. Therefore, Formulation A falls within the scope of the invention. Formulations B and C fall outside the scope of the invention. The particle size distribution of the formulations is found in Table 2, below. The particle size is measured by the laser diffraction method using a Malvern Mastersizer 2000.

TABLE 2

| | Formulation A | Formulation B/C |
|---|---|---|
| d10 (µm) | 1.764 | 3.039 |
| d50 (µm) | 5.578 | 16.690 |
| d90 (µm) | 15.190 | 89.081 |
| Span | 2.41 | 5.16 |

It is important to note that not only is the d50 and the d90 of Formulation A significantly smaller than the d50 and d90 of Formulations B and C, but the span between the d50 and d90 of Formulation A (i.e., d50 5.578 µm and d90 15.190

μm) and the span between d50 and d90 of Formulations B and C (i.e., d50 16.690 μm and d90 89.081 μm) is significantly smaller as well.

Example 1

Figure 2:
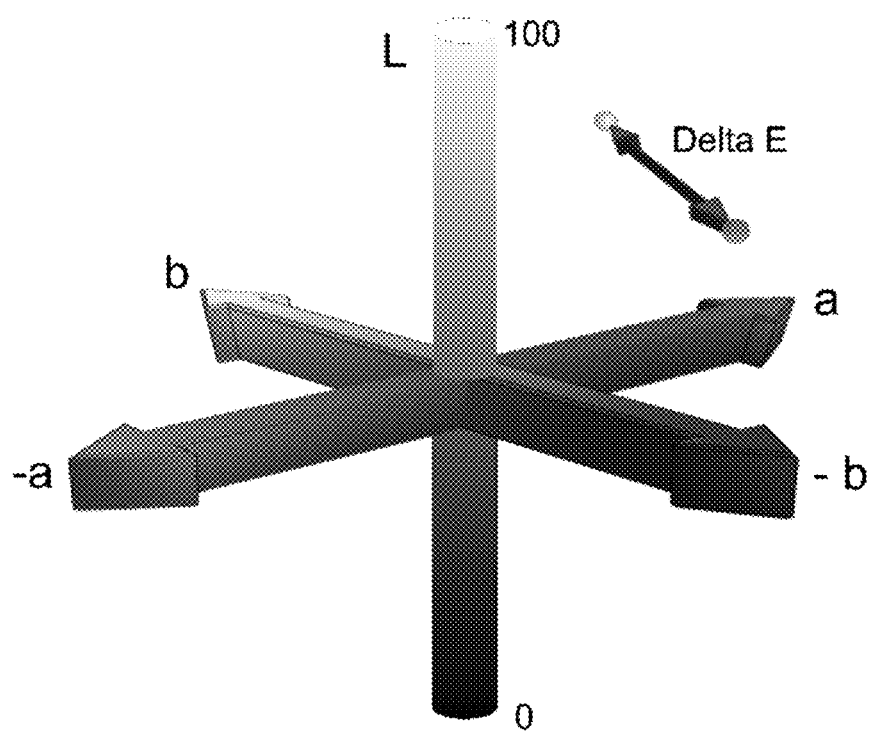
FIG. 2 depicts a CIELAB Color Space Diagram (CIE L*a*b* (CIELAB) is a color space specified by the International Commission on Illumination (French Commission internationale de l'eclairage, hence its CIE initialism). It describes all the colors visible to the human eye and was created to serve as a device-independent model to be used as a reference).

Color was quantitatively measured with a spectrophotometer and color changes were expressed by using the CIELAB color parameters (a*, b*, L* and ΔE*). L* represents the lightness from white (100) to black (0). a* is green (−a*) to red (+a*) and b* is blue (−b*) to yellow (+b*). FIG. 2 represents the CIELAB color space three-dimensional diagram. The total color differences parameter ΔE* were calculated from the initial conditions before heat treatment and represents the Euclidean distance between two points in three dimensional CIELAB color space:

$$\Delta a^* = a^* - a_0^*,$$

$$\Delta b^* = b^* - b_0^*,$$

$$\Delta L^* = L^* - L_0^*,$$

$$\Delta E^* = \sqrt{\Delta a^{*2} + \Delta b^{*2} + \Delta L^{*2}}.$$

A ΔE*≈2.3 (approximately 2.3) corresponds to a just noticeable difference (JND) which is defined as the amount the color must be changed in order for the difference in color to be noticeable. (Sharma, Gaurav (2003), Digital Color Imaging Handbook (1.7.2 ed.), CRC Press. ISBN 0-8493-0900-X.

The following measurement method was used:
Equipment: Colorflex-EZ available from HunterLab;
Mode: Reflectance.
Two readings were taken for each recorded measurement.
Scale used was L*a*b*, at a setting of D65/10.
Before being characterized, the samples were stored in 60 mL brown glass bottles under the following conditions:
Temperature 5° C. representing reference conditions (very limited discoloration expected at this temperature);
Temperature 25° C.;
Temperature 40° C./representing accelerated testing conditions.

Each bottle had the same head space to minimize differences due to oxidation.

Figure 3:
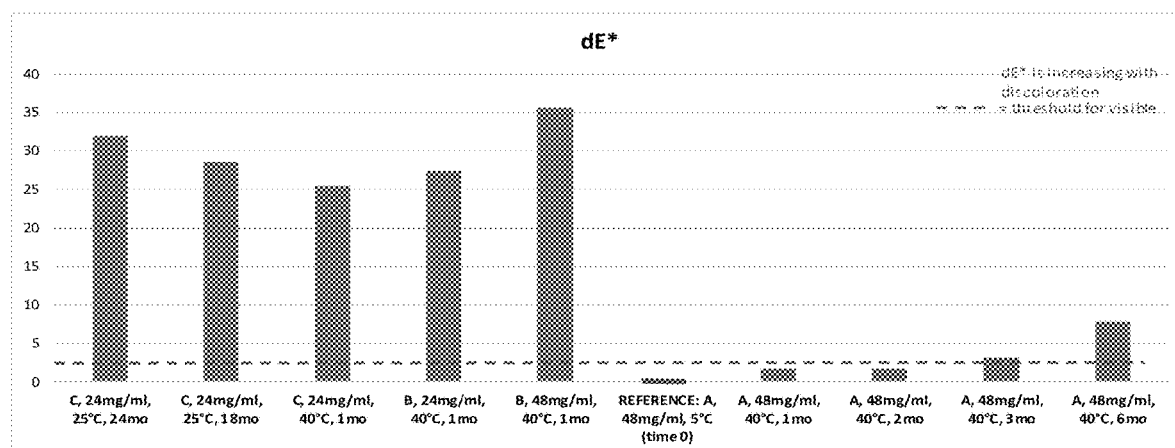
FIG. 3 is a graphical depiction of a color change comparison, defined by ΔE* values, for the analyzed samples including Formulation A, Formulation B and Formulation C.

In Example 1, reference Formulation A contained 48 mg/100 mL suspension of paracetamol and 0.0% wt./v of methyl or propyl paraben preservatives. The results shown in FIG. 3 depict color trends for a maximum storage time of 6 months. According to FIG. 3, ΔE* increases with storage temperature and time. The threshold of visible difference, i.e., when a visible color change or JND can be detected is represented by the dotted line. At time 0 and temperature of 5° C., a 48 mg/100 mL paracetamol suspension of reference Formulation A had no visible color change. As depicted in FIG. 3, under accelerated stability conditions of 40° C., reference Formulation A had no visible color change at 1 or 2 months. In contrast, a 48 mg/100 mL paracetamol suspension of reference Formulation B at 40° C. for 1 month has a ΔE* of about 35 in FIG. 3. For reference Formulation A, a visible color change can only be marginally appreciated under accelerated stability conditions of 3 months at 40° C. Further, even under accelerated stability conditions of 6 months and 40° C., the color change, ΔE*, of reference Formulation A is still only about 7 to 8. As depicted in FIG. 3, the color change, ΔE* perceived for reference Formulation A is significantly lower than color change, ΔE* perceived for reference Formulations B and C under accelerated stability conditions. In terms of the change in color over time, Formulation A is clearly superior and thus, advantageous to Formulations B and C.

Example 2

Using the same conditions and instrument(s) as in Example 1, additional color measurements were generated. In Example 2, Formulation A contained a 4.8 g/100 mL of suspension (48 mg/mL) of paracetamol and 0.2 g/100 mL of suspension of methyl paraben and 0.045 g/100 mL of suspension of propyl paraben preservatives. Formulation B contained 4.8 g/100 mL of suspension (48 mg/mL) of paracetamol.

The results of color measurements for samples of Formulation A and Formulation B are shown in Table 3, below. The Formulation A sample at time 0 was taken as a reference for the ΔE* calculation.

TABLE 3

| Formulation | L* | a* | b* | ΔL* | Δa | Δb* | ΔE* |
|---|---|---|---|---|---|---|---|
| Formulation A 48 mg/ml at time 0 | 82.68 | −0.52 | 2.8 | 0.00 | 0.00 | 0.00 | 0 |
| Formulation A 48 mg/ml, at 3M 25° C. | 81.9 | −0.18 | 4.33 | −0.78 | 0.34 | 1.53 | 1.75 |
| Formulation A 48 mg/ml, at 3M 40° C. | 75.97 | 1.46 | 7.96 | −6.71 | 1.98 | 5.16 | 8.69 |
| Formulation B, 48 mg/ml at time 0 | 67.14 | −0.59 | −2.49 | −15.54 | −0.07 | −5.29 | 16.42 |
| Formulation B 48 mg/ml at 3M 40° C. | 51.18 | 1.94 | 10.89 | −31.5 | 2.46 | 8.09 | 32.62 |

The results of color measurements for samples of Formulation A, Formulation B and Formulation C, each with a paracetamol concentration of 24 mg/ml are shown in Table 4, below. The Formulation A sample at time 0 was taken as a reference for the ΔE* calculation.

TABLE 4

| Formulation | L* | a* | b* | ΔL* | Δa* | Δb* | ΔE* |
|---|---|---|---|---|---|---|---|
| Formulation A 24 mg/ml at time 0 | 70.55 | −1.07 | 2.2 | 0 | 0 | 0 | 0.00 |
| Formulation A 24 mg/ml at 3M, 25° C. | 63.03 | −0.54 | 2.74 | −7.52 | 0.53 | 0.54 | 7.56 |

TABLE 4-continued

| Formulation | L* | a* | b* | ΔL* | Δa* | Δb* | ΔE* |
|---|---|---|---|---|---|---|---|
| Formulation A 24 mg/ml at 3M, 40° C. | 48.01 | 1.34 | 6.11 | −22.54 | 2.41 | 3.91 | 23.00 |
| Formulation C 3M, at 40° C. | 40.94 | 2.2 | 6.3 | −29.61 | 3.27 | 4.1 | 30.07 |
| Formulation B 3M, at 40° C. | 38.32 | 2.3 | 10.85 | −32.23 | 3.37 | 8.65 | 33.54 |

Based on the values shown in Table 3 and Table 4, for a given paracetamol concentration and under the same storage conditions, Formulation A showed less color change than the Formulation B and Formulation C samples, for a given storage condition. While at a concentration of 48 mg/mL, accelerated stability conditions of 3 months at 40° C., Formulation A has a ΔE* of 8.69 which is above the threshold of JND (ΔE*≈2.3), this ΔE* is significantly lower than the ΔE* of 32.62 for Formulation B under the same accelerated stability conditions. These accelerated stability conditions of 3 months at 40° C., are representative of a shelf life of greater than about 36 months.

This result is more evident for Formulation A at the highest paracetamol concentration of 48 mg/mL as can be seen by comparing ΔE* values of Tables 3, where at time 0, Formulation A had a ΔE* of 0 and Formulation B had a ΔE* of 16.42. Nonetheless, at the lower concentration of paracetamol, 24 mg/ml, Formulation A samples are still less dark when compared with Formulation B and Formulation C samples, even though the difference in color is less pronounced at this concentration. The difference between formulations is higher than analytical variability (about ΔE*=±1)

Figure 4A:
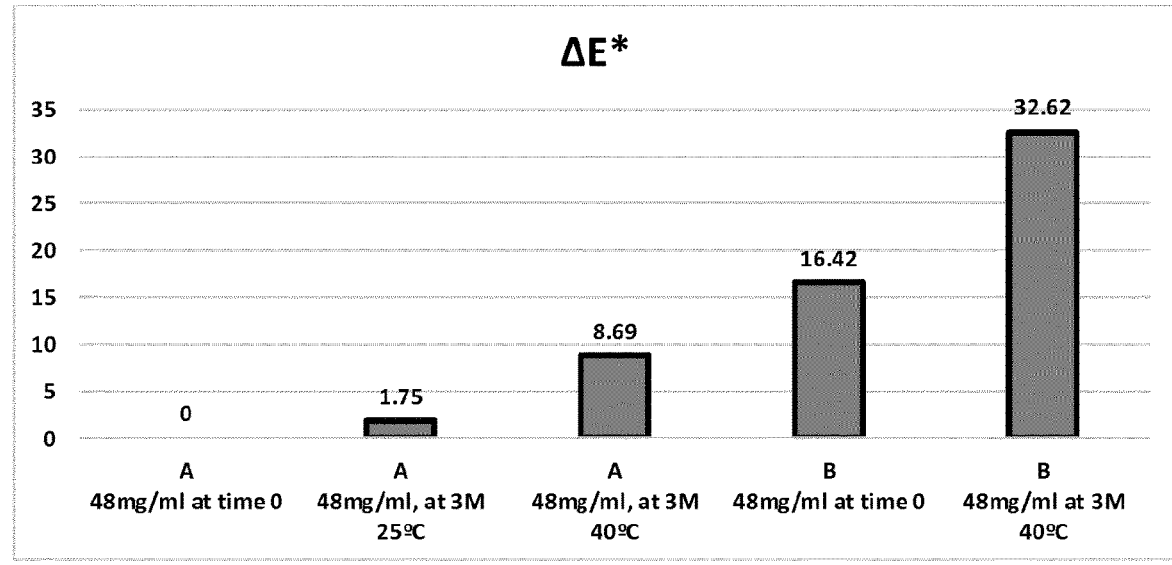
FIG. 4A is a graphical depiction of the total color difference ΔE* for Formulation A and Formulation B at a paracetamol concentration of 48 mg/mL. The Formulation A sample just after manufacturing is taken as reference.
Figure 4B:
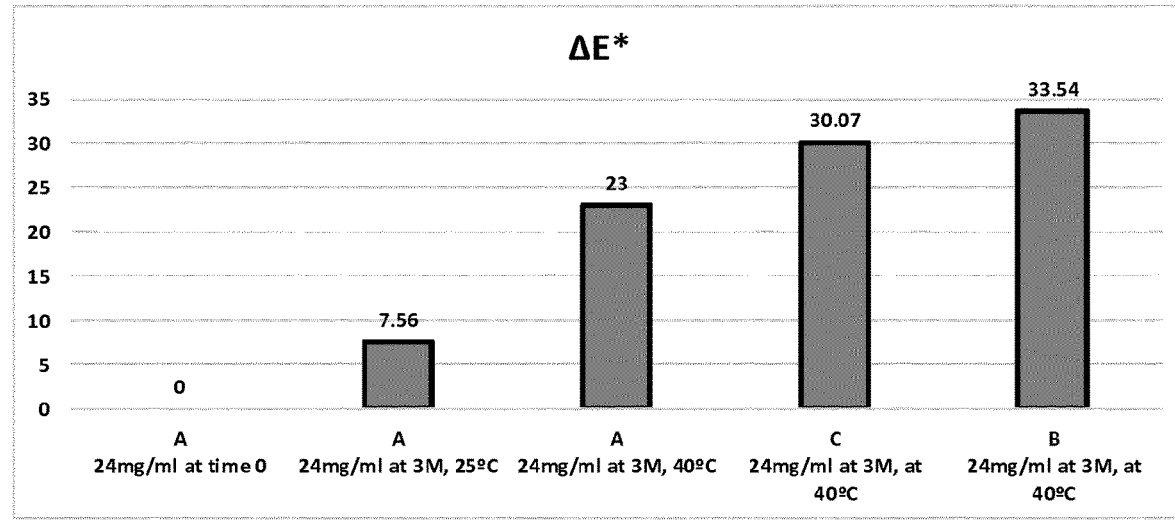
FIG. 4B is a graphical depiction of the total color difference ΔE* for Formulation A, Formulation B and Formulation C at a paracetamol concentration of 24 mg/ml. The Formulation A sample just after manufacturing is taken as reference.

These results are depicted in graphical format in FIG. 4A and FIG. 4B.

Example 3

Figure 5:
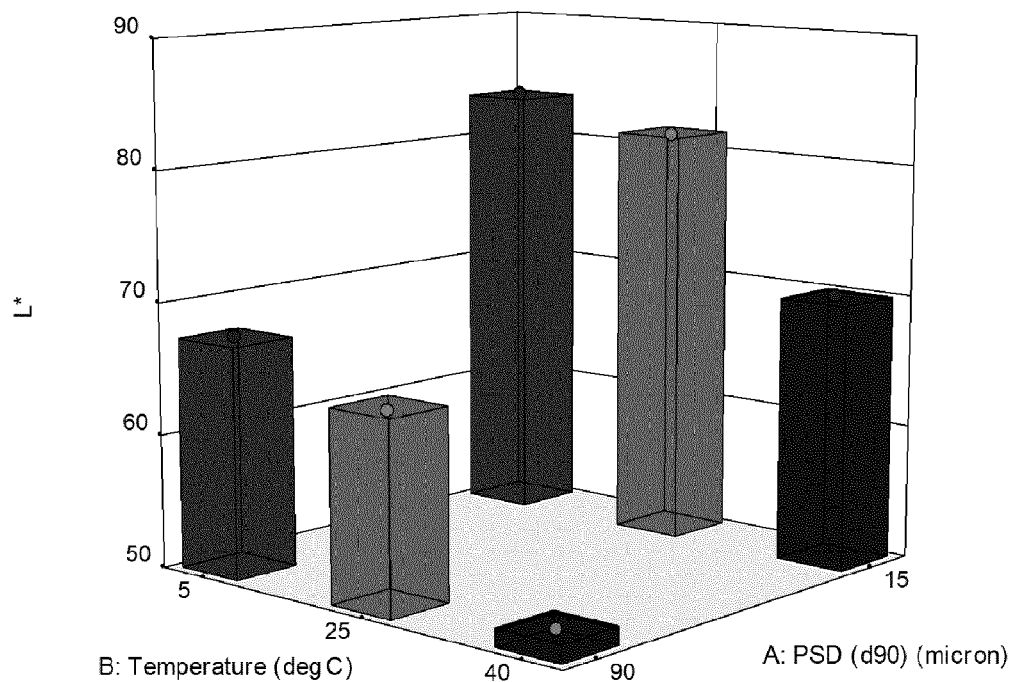
FIG. 5 depicts the impact of paracetamol particle size and storage temperature on color measurements in terms of lightness L* for samples taken at 9 months.

In Example 3, reference Formulation A contained 48 mg/mL suspension of paracetamol and 0.0% wt./v of methyl or propyl paraben preservatives. Formulation A samples were manufactured with two different paracetamol particle size grades: microfine grade (i.e., d10 1.764 μm, d50 5.578 μm and d90 15.190 μm) and extra dense grade (i.e., d10 3.039 μm, d50 16.690 μm and d90 89.081 μm). The samples were stored at different temperature conditions and measurements were taken at different time points (latest measurements at storage time of 9 months). The bottles containing the samples had the same head space. Results were analyzed with Design-Expert software (commercially available from Stat-Ease Inc.). Color measurements for samples taken at 9 months are shown in FIG. 5. Measurements of samples taken at 6 months show similar trends. According to the conditions above, an experimental plan with 3 variables and mixed levels was built with the parameters in Table 5, below.

TABLE 5

| | Paracetamol particle size - d90 (μm) | Storage temperature (° C.) |
|---|---|---|
| Minimum level | 15 | 5 |
| Medium level | — | 25 |
| Maximum level | 80 | 40 |

FIG. 5 depicts particle size distribution (PSD) along axis A, Temperature along axis B, and L* (the lightness from white (100) to black (0)) along axis Y. As the L* value increases, more light is visible through the formulation and it appears whiter. As the L* value decreases, less light is visible through the formulation and it appears darker and brown. For the extra dense grade version of reference Formulation A (d90 89.081 μm rounded to 90 μm) at Temperature 5° C., the L* value was about 67; at Temperature 25° C., the L* value was about 59; and at Temperature 40° C., the L* value was about 51. Therefore, for the extra dense grade version of reference Formulation A as the temperature increases, the L* value decreases and the suspension appeared visibly darker and brown in color. For the microfine grade version of reference Formulation A (d90 about 15 μm) at Temperature 5° C., the L* value was about 83; at Temperature 25° C., the L* value was about 81; and at Temperature 40° C., the L* value was about 69. Therefore, for the microfine grade version of reference Formulation A the L* value did not change significantly from 5° C. to 25° C. and the suspension appeared visibly white. And, at as the temperature increased to 40° C., the L* value of about 69 is still higher, and the suspension is therefore whiter, when compared with the L* value of about 67 for extra dense grade version of Formulation A at 5° C. As observed in previous measurements, lightness L* variation was primarily accountable for the total color difference. For any storage temperature, lightness L* is consistently higher with finer paracetamol particle size, thus indicating a less discolored product.

Example 4

Using the same conditions and instrument(s) as in Example 1, additional color measurements were generated. In Example 4, Formulation A contained a 4.8 g/100 mL of suspension (48 mg/mL) of paracetamol. Formulation B contained 4.8 g/100 mL of suspension (48 mg/mL) of paracetamol.

The results of color measurements for samples of Formulation A and Formulation B are shown in Table 6, below. The Formulation A (48 mg/mL) sample at time 0 was taken as a reference for the ΔE* calculation.

TABLE 6

| Formulation | L* | a* | b* | ΔL* | Δa* | Δb* | ΔE* |
|---|---|---|---|---|---|---|---|
| Formulation A 48 mg/ml at time 0 | 82.68 | −0.52 | 2.8 | 0.00 | 0.00 | 0.00 | 0.00 |
| Formulation A 48 mg/ml at 3-months, 25° C. | 81.9 | −0.18 | 4.33 | −0.78 | 0.34 | 1.53 | 1.75 |

TABLE 6-continued

| Formulation | L* | a* | b* | ΔL* | Δa* | Δb* | ΔE* |
|---|---|---|---|---|---|---|---|
| Formulation A 48 mg/ml at 3-months, 40° C. | 75.97 | 1.46 | 7.96 | −6.71 | 1.98 | 5.16 | 8.69 |
| Formulation B 48 mg/ml at time 0 | 67.14 | −0.59 | −2.49 | −15.54 | −0.07 | −5.29 | 16.42 |
| Formulation B 48 mg/ml at 3-months, 25° C. | 66.39 | −1.01 | 5.42 | −16.29 | −0.49 | 2.62 | 16.51 |
| Formulation B 48 mg/ml at 3-months, 40° C. | 51.18 | 1.94 | 10.89 | −31.5 | 2.46 | 8.09 | 32.62 |

Figure 6:
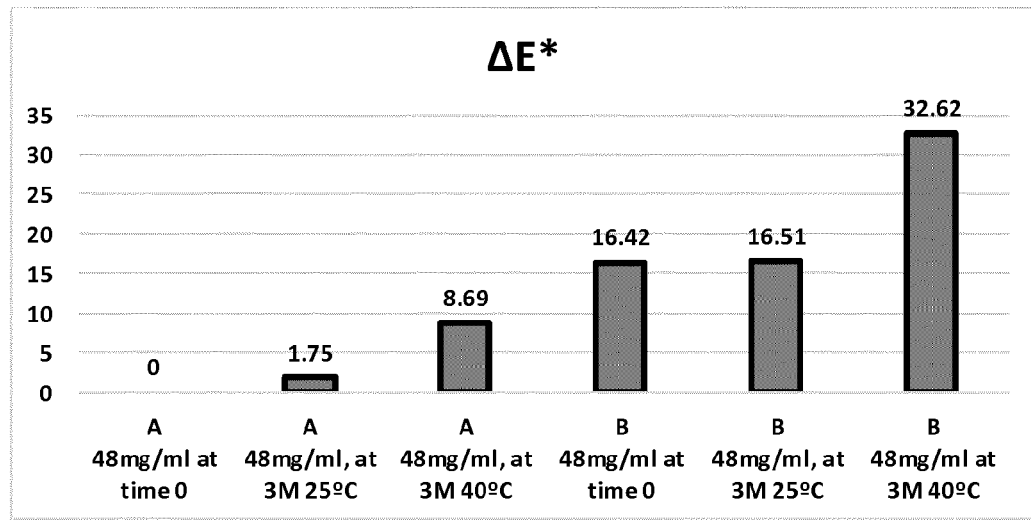
FIG. 6 is a graphical depiction of the total color difference ΔE* for Formulation A and Formulation B at a paracetamol concentration of 48 mg/ml. The Formulation A sample just after manufacturing is taken as reference.

Based on the results shown in Table 6, samples of Formulation A (48 mg/ml) were confirmed to be less dark compared to samples of Formulation B (48 mg/ml) for a given storage condition. This conclusion is confirmed also after a 3-months storage at 25° C. and demonstrated by a ΔE* of 1.75 for Formulation A, against a ΔE* of 16.51 for Formulation B. These results are depicted in graphical format in FIG. 6.

Example 5

Using the same conditions and instrument(s) as in Example 1, additional color measurements were generated. The results of color measurements for samples of Formulation A, Formulation B and Formulation C, each with a paracetamol concentration of 24 mg/ml are shown in Table 7, below. The Formulation A (24 mg/ml) sample at time 0 was taken as a reference for the ΔE* calculation.

TABLE 7

| Formulation | L* | a* | b* | ΔL* | Δa* | Δb* | ΔE* |
|---|---|---|---|---|---|---|---|
| Formulation A 24 mg/ml at time 0 | 70.55 | −1.07 | 2.2 | 0 | 0 | 0 | 0 |
| Formulation A 24 mg/ml at 3-months, 25° C. | 63.03 | −0.54 | 2.74 | −7.52 | 0.53 | 0.54 | 7.56 |
| Formulation A 24 mg/ml at 3-months, 40° C. | 48.01 | 1.34 | 6.11 | −22.54 | 2.41 | 3.91 | 23.00 |
| Formulation B 24 mg/ml at time 0 | 48.25 | −0.5 | −1.51 | −22.3 | 0.57 | −3.71 | 22.61 |
| Formulation B 24 mg/ml at 3-months, 25° C. | 49.03 | −0.39 | 0.02 | −21.52 | 0.68 | −2.18 | 21.64 |
| Formulation B 24 mg/ml at 3-months, 40° C. | 43.13 | 0.5 | 6.38 | −27.42 | 1.57 | 4.18 | 27.78 |
| Formulation C 24 mg/ml at time 0 | 51.31 | −0.78 | −1.47 | −19.24 | 0.29 | −3.67 | 19.59 |
| Formulation C 24 mg/ml at 3-months, 25° C. | 51.2 | −0.49 | −0.62 | −19.35 | 0.58 | −2.82 | 19.56 |
| Formulation C 24 mg/ml at 3-months, 40° C. | 42.94 | 1.32 | 3.92 | −27.61 | 2.39 | 1.72 | 27.77 |

Figure 7:
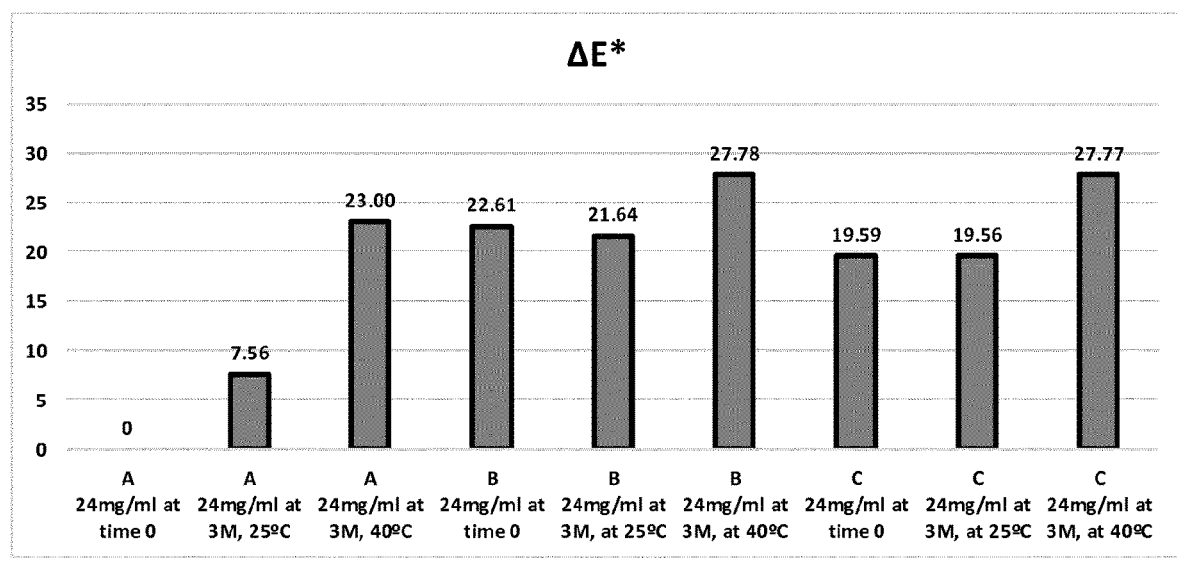
FIG. 7 is a graphical depiction of the total color difference ΔE* for Formulation A and Formulation B and Formulation C at a paracetamol concentration of 24 mg/ml. The Formulation A sample just after manufacturing is taken as reference.

Based on the results shown in Table 7, samples of Formulation A (24 mg/ml) are confirmed to be less dark to samples of Formulation B (24 mg/ml) and Formulation C (24 mg/ml) for a given storage condition. This conclusion is confirmed (a) at time 0, (b) after 3-months storage at 25° C. and (c) after 3-months storage at 40° C., and it is demonstrated by a ΔE* values that are lower for Formulation A at each given storage condition. These results are depicted in graphical format in FIG. 7.

Example 6

Using the same conditions and instrument(s) as in Example 1, additional color measurements were generated. In Example 6, Formulation A contained a 4.8 g/100 mL of suspension (48 mg/mL) of paracetamol and was tested for color (a) after 3-months storage at 40° C. and (b) after 27-months storage at ambient temperature 15-25° C. (conditions that are representative of end of shelf life).

The results of color measurements for samples of Formulation A are shown in Table 8, below. The Formulation A (48 mg/mL) sample at time 0 was taken as a reference for the ΔE* calculation.

TABLE 8

| Formulation | L* | a* | b* | ΔL* | Δa* | Δb* | ΔE* |
|---|---|---|---|---|---|---|---|
| Formulation A 48 mg/ml at time 0 | 82.68 | −0.52 | 2.8 | 0 | 0 | 0 | 0 |
| Formulation A 48 mg/ml at 3-months, 40° C. | 75.97 | 1.46 | 7.96 | −6.71 | 1.98 | 5.16 | 8.69 |

TABLE 8-continued

| Formulation | L* | a* | b* | ΔL* | Δa* | Δb* | ΔE* |
|---|---|---|---|---|---|---|---|
| Formulation A 48 mg/ml at 27-months, 15-25° C. | 78.14 | 0.66 | 7.65 | −4.54 | 1.18 | 4.85 | 6.75 |

As can be seen in Table 8, the results show similar ΔE* values for Formulation A after 3-months storage at 40° C. and same Formulation A after 27-months storage at 15-25° C. (conditions that are representative of end of shelf life).

Based on these results, results of color measurements after 3-months storage at 40° C. can be considered indicative of end of shelf life.

What is claimed is:

1. A pharmaceutical composition comprising a liquid suspension having paracetamol particles with a d50 of less than or equal to 10 μm and a d90 of less than or equal to 35 μm,
wherein the composition is substantially dye-free and substantially free of reducing sugars.

2. The pharmaceutical composition according to claim 1, wherein the paracetamol concentration is 24 mg/ml.

3. The pharmaceutical composition according to claim 1, wherein the paracetamol concentration is 32 mg/ml.

4. The pharmaceutical composition according to claim 1, wherein the paracetamol concentration is 48 mg/ml.

5. A pharmaceutical composition according to claim 1 comprising a high intensity sweetener selected from sucralose, aspartame, saccharin, acesulfame, cyclamate, and pharmaceutically acceptable salts thereof.

6. A pharmaceutical composition according to claim 5 wherein the high intensity sweetener is sucralose.

7. A pharmaceutical composition according to claim 1 comprising a polyhydric alcohol sweetener selected from sorbitol, mannitol, xylitol erythritol, maltitol and a combination of at least two or more thereof.

8. A pharmaceutical composition according to claim 7 wherein the polyhydric alcohol sweetener is a combination of sorbitol and maltitol.

9. A pharmaceutical composition according to claim 1 comprising an antimicrobial preservative selected from methyl paraben, propyl paraben, sodium methyl paraben, sodium ethyl paraben, sodium propyl paraben and a combination of two or more thereof.

10. A pharmaceutical composition according to claim 9 wherein the antimicrobial preservative is a combination of methyl paraben and propyl paraben.

11. A pharmaceutical composition according to claim 1 comprising a thickening agent which is xanthan gum.

12. A pharmaceutical composition according to claim 1 comprising a humectant selected from glycerine, sorbitol, polyethylene glycol, propylene glycol and a combination of two or more thereof.

13. A pharmaceutical composition according to claim 12 wherein the humectant is glycerine.

14. The pharmaceutical composition according to claim 1, wherein the composition has a total color differences parameter ΔE* value after 27-months storage at 15-20° C. of less than 10 according to CIELAB color parameters.

15. A pharmaceutical composition comprising a liquid suspension having:
2.0-5.0% wt./v paracetamol;
0.50-1.00% wt./v xanthan gum;
10-20% wt./v glycerine;
10-20% wt./v sorbitol 70% solution;
50-60% wt./v maltitol;
0.020-0.030% wt./v anhydrous citric acid;
0.20-0.30% wt./v sodium citrate dihydrate;
0.20-0.40% wt./v sucralose; and
q.s. to 100% wt./v water,
wherein the paracetamol is present as suspended particles with a d50 of less than or equal to 10 μm and a d90 of less than or equal to 35 μm, and
wherein the composition is substantially dye-free and substantially free of reducing sugars.

16. The pharmaceutical composition of claim 15, wherein the composition has a total color differences parameter ΔE* value after 27-months storage at 15-20° C. of less than 10 according to CIELAB color parameters.

17. The pharmaceutical composition of claim 15, wherein the composition further comprises 0.01-0.20% wt./v methyl paraben, 0.01-0.065% wt./v propyl paraben, or a combination of both.

18. The pharmaceutical composition of claim 15, wherein the composition further comprises 0.005-0.015% wt./v EDTA.

19. The pharmaceutical composition of claim 15 further comprising a flavoring agent.

* * * * *